United States Patent
Shih

(10) Patent No.: US 11,696,380 B2
(45) Date of Patent: Jul. 4, 2023

(54) LIGHTING FIXTURE AND LIGHTING SYSTEM FOR AUTOMATICALLY ADJUSTING COLOR TEMPERATURE

(71) Applicant: Test Rite International Co., Ltd., Taipei (CN)

(72) Inventor: Agnes Shih, Taipei (CN)

(73) Assignee: Test Rite International Co., Ltd., Taipei (CN)

( * ) Notice: Subject to any disclaimer, the term of this patent is extended or adjusted under 35 U.S.C. 154(b) by 297 days.

(21) Appl. No.: 17/240,974

(22) Filed: Apr. 26, 2021

(65) Prior Publication Data

US 2022/0346200 A1 Oct. 27, 2022

(51) Int. Cl.
*H05B 45/20* (2020.01)
*H05B 47/13* (2020.01)
*H05B 47/11* (2020.01)
*A61B 5/01* (2006.01)

(52) U.S. Cl.
CPC ............. *H05B 45/20* (2020.01); *A61B 5/01* (2013.01); *H05B 47/11* (2020.01); *H05B 47/13* (2020.01)

(58) Field of Classification Search
CPC ........ H05B 45/20; H05B 47/11; H05B 47/13; A61B 5/01
See application file for complete search history.

(56) References Cited

U.S. PATENT DOCUMENTS

2013/0134902 A1* 5/2013 Mahale ................ H05B 47/115
315/297

* cited by examiner

*Primary Examiner* — Alexander H Taningco
*Assistant Examiner* — Pedro C Fernandez
(74) *Attorney, Agent, or Firm* — Bayramoglu Law Offices LLC

(57) ABSTRACT

The present invention provides a lighting fixture and lighting system for automatically adjusting a color temperature. The optimal color temperature is obtained by adjusting step by step using the light intensity, the infrared movement signal, the visibility, the human body temperature and the environment temperature. Specifically, the color temperature is compensated for and adjusted by the light sources of at least two light emitting units. In this way, the adjustment range of the color temperature is extended, making it possible to obtain the optimal color temperature.

8 Claims, 2 Drawing Sheets

---

Obtaining a light intensity and an infrared movement signal to determine whether to start lighting;

↓

Obtaining visibility information, constructing a current visibility model according to the visibility information to obtain a visibility, and determining a first color temperature parameter according to the visibility;

↓

Obtaining human body temperature data, and adjusting the first color temperature parameter according to the human body temperature data to obtain a second color temperature parameter; and

↓

Obtaining environment temperature data, and adjusting the second color temperature parameter according to the environment temperature data to obtain a final color temperature parameter.

LIGHTING FIXTURE AND LIGHTING SYSTEM FOR AUTOMATICALLY ADJUSTING COLOR TEMPERATURE

TECHNICAL FIELD

The present invention relates to the technical field of lighting technology, and more particularly, to a lighting fixture and lighting system for automatically adjusting a color temperature.

BACKGROUND

With the advancement of science and technology and the improvement of the quality of life, people desire a broader range of properties and requirements of light-emitting diodes (LEDs) as a source of illumination. In order to achieve energy savings, for example, it is desirable to freely adjust the brightness of the light. In order to create a variable atmosphere, on the other hand, it is desirable to adjust the color of illumination from a light source so as to elicit in a human body a feeling of temperature and set the lighting environment according to one's preference.

In the prior art, color temperature or brightness is changed by adjusting the drive current. In particular, the color temperature is adjusted artificially depending merely on the feelings of the user, is not accurate enough. To solve this issue in the prior art, the environment temperature is used to perform a further adjustment, but the environment temperature is not the only factor involved in the adjustment of color temperature.

Therefore, it is highly desirable to provide a lighting fixture and lighting system for automatically adjusting the color temperature accurately.

SUMMARY

In view of the above-mentioned issue, the present invention provides a lighting fixture and lighting system for automatically adjusting a color temperature according to a preset priority, thereby accurately adjusting the color temperature.

In order to achieve the above-mentioned objective, the present invention provides the following technical solutions.

A lighting method for automatically adjusting a color temperature includes the following specific steps:

obtaining a light intensity and an infrared movement signal to determine whether to start lighting;

obtaining visibility information, constructing a current visibility model according to the visibility information to obtain a visibility, and determining a first color temperature parameter according to the visibility;

obtaining human body temperature data, and adjusting the first color temperature parameter according to the human body temperature data to obtain a second color temperature parameter; and obtaining environment temperature data, and adjusting the second color temperature parameter according to the environment temperature data to obtain a final color temperature parameter.

Preferably, in the aforementioned lighting method for automatically adjusting the color temperature, the visibility information includes one or more of a solid particle concentration, a droplet concentration and an atmospheric pressure.

Preferably, in the aforementioned lighting method for automatically adjusting the color temperature, the step of constructing the current visibility model specifically includes the following steps:

obtaining a data image and a visibility value according to historical data;

inputting the data image and the visibility value into a neural network model;

training the neural network model to obtain a weight of the visibility information; and obtaining the current visibility model according to the weight.

Preferably, in the aforementioned lighting method for automatically adjusting the color temperature, a current visibility level is obtained according to the current visibility model, and the visibility level is configured to match the first color temperature parameter.

A lighting system for automatically adjusting a color temperature includes light emitting units, a drive device, and a data acquisition and analysis unit. The number of the light emitting units is at least two. The data acquisition and analysis unit feeds an analysis result back to the drive device. The drive device drives the at least two light emitting units, respectively. The at least two light emitting units generate light sources with different color temperatures to compensate for each other.

Preferably, in the aforementioned lighting system for automatically adjusting the color temperature, the drive device includes a processor and a driver circuit. The processor acquires the analysis result of the data acquisition and analysis unit and adjusts a magnitude or a duty cycle of a drive current generated by the driver circuit. Drive currents input to the at least two light emitting units are different.

Preferably, in the aforementioned lighting system for automatically adjusting the color temperature, the data acquisition and analysis unit includes a light detection unit, a visibility detection unit, a human body temperature measurement unit, and an environment measurement unit. The light detection unit detects a light intensity. The visibility detection unit detects a visibility value. The human body temperature measurement unit measures a body temperature of a user. The environment measurement unit measures an environment temperature.

Preferably, in the aforementioned lighting system for automatically adjusting the color temperature, the data acquisition and analysis unit further includes an infrared movement signal detection unit. The infrared movement signal detection unit detects the presence or movement of a human body, and converts an output signal into a voltage signal.

Preferably, in the aforementioned lighting system for automatically adjusting the color temperature, the data acquisition and analysis unit sends the acquired data information to the processor. The processor calculates a color temperature parameter adapted to a current data state according to a built-in algorithm, and controls the driver circuit to adjust the light sources.

Preferably, the aforementioned lighting system for automatically adjusting the color temperature further includes a manual adjustment unit, and the manual adjustment unit is arranged between the light emitting units and the driver circuit.

According to the above technical solutions, compared with the prior art, the present invention provides a lighting fixture and lighting system for automatically adjusting a color temperature. The optimal color temperature is obtained by adjusting step by step using the light intensity, the infrared movement signal, the visibility, the human body temperature and the environment temperature. Specifically, the color temperature is compensated for and adjusted by the light sources of at least two light emitting units. In this way, the adjustment range of the color temperature is extended, making it possible to obtain the optimal color temperature.

BRIEF DESCRIPTION OF THE DRAWINGS

In order to more clearly illustrate the technical solutions in the embodiments of the present invention or the prior art, the drawings used in the embodiments or the prior art will be described briefly below. Obviously, the drawings described below are only used as embodiments of the present invention. For those having ordinary skill in the art, other drawings may be obtained according to the drawings without creative efforts.

DETAILED DESCRIPTION OF THE EMBODIMENTS

In order to make the objectives, technical solutions and advantages of the embodiments of the present invention more clear, the technical solutions in the embodiments of the present invention will be described clearly and completely in combination with the drawings in the embodiments of the present invention. Obviously, the described embodiments are only a part of the embodiments of the present invention, rather than all of the embodiments. Based on the embodiments of the present invention, all other embodiments obtained by those having ordinary skill in the art without creative efforts shall fall within the scope of the protection of the present invention.

Figure 1:
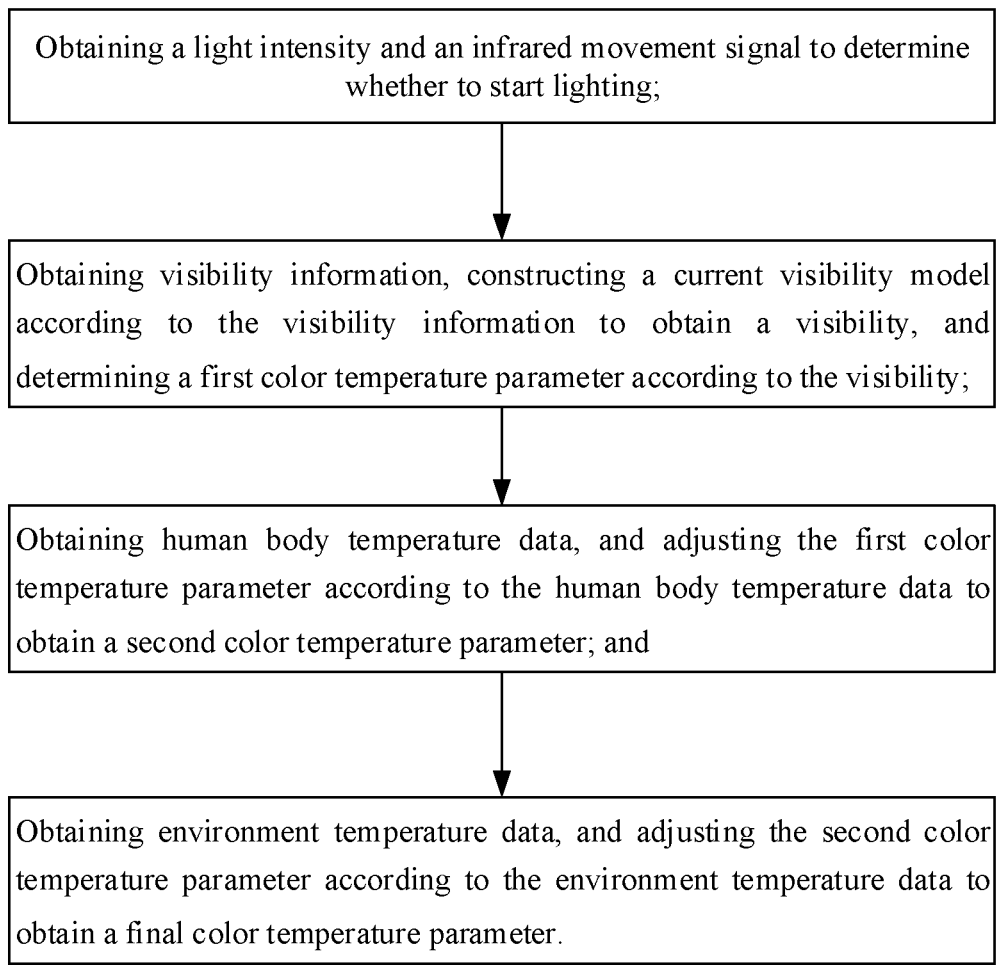
FIG. 1 is a flow chart of the method of the present invention.

According to an embodiment of the present invention, as shown in FIG. 1, a lighting method for automatically adjusting a color temperature includes the following specific steps:

a light intensity and an infrared movement signal are obtained to determine whether to start lighting;

visibility information is obtained, a current visibility model is constructed according to the visibility information to obtain a visibility, and a first color temperature parameter is determined according to the visibility;

human body temperature data are obtained, and the first color temperature parameter is adjusted according to the human body temperature data to obtain a second color temperature parameter; and environment temperature data are obtained, and the second color temperature parameter is adjusted according to the environment temperature data to obtain a final color temperature parameter.

It is known that light with a color temperature of lower than 3500 K is typically defined as warm light, which can elicit in a human body a warm and comfortable feeling. Light with a color temperature of around 3600 K-5000 K is defined as white light, which is soft and thus can elicit in a human body a pleasant, comfortable and serene feeling. Light with a color temperature of higher than 5000 K is defined as cold light, whose light source is close to natural light and elicits in a human body a bright feeling.

Further, it is determined whether to start lighting according to the light intensity. The first color temperature parameter is determined according to a current visibility value. For example, warm light is used when the current visibility is low, and adjustment is performed according to the second color temperature parameter when the visibility is normal. The second color temperature parameter is determined according to the human body temperature data. For example, warm light is used when the human body temperature is lower than 36 degrees Celsius, cold light is used when the human body temperature is higher than 37 degrees Celsius, and adjustment is performed according to the third color temperature parameter when the human body temperature is normal. The third color temperature parameter is determined according to the current environment temperature. For example, warm light is used when the environment temperature is lower than 12 degrees Celsius, cold light is used when the environment temperature is higher than 30 degrees Celsius, and white light is used when the environment temperature is between 12 degrees Celsius and 30 degrees Celsius.

Specifically, the final color temperature parameter is determined by constructing a mathematical model, such as a mathematical model of color temperature-influence factor, so that the optimal color temperature parameter matched with the current state is determined through the above model.

Optimally, the visibility information includes one or more of a solid particle concentration, a droplet concentration and an atmospheric pressure.

Further, the visibility information is obtained through a sensor, and is not limited to the above factors. For example, the light intensity will also affect the visibility.

Optimally, the step of constructing the current visibility model specifically includes the following steps:

a data image and a visibility value are obtained according to historical data;

the data image and the visibility value are input into a neural network model;

the neural network model is trained to obtain a weight of the visibility information; and the current visibility model is obtained according to the weight.

Further, in the present embodiment, an existing neural network model, such as a multi-layer perceptron (MLP) neural network-based visibility prediction model, is employed and trained according to the historical data. Finally, the trained neural network model is used to determine the visibility level.

Optimally, the current visibility level is obtained according to the current visibility model, and the visibility level is configured to match the first color temperature parameter.

Further, a mapping relationship between the visibility level and the color temperature parameter is determined according to the historical data, so that the color temperature parameter is determined according to the current visibility model.

Figure 2:
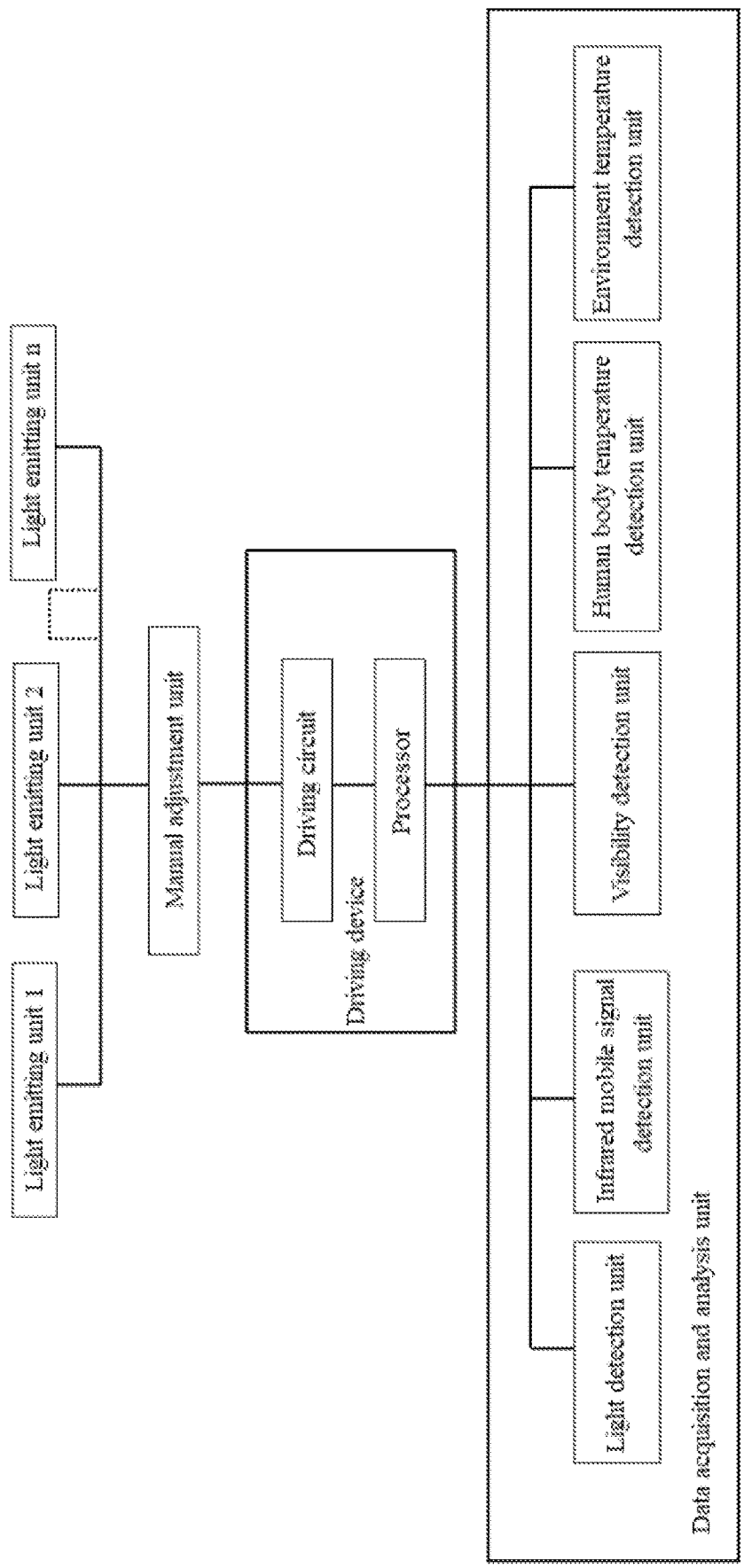
FIG. 2 is a block diagram of the structure of the present invention.

According to an embodiment of the present invention, as shown in FIG. 2, a lighting system for automatically adjusting a color temperature includes light emitting units, a drive device, and a data acquisition and analysis unit. The number of the light emitting units is at least two. The data acquisition and analysis unit feeds an analysis result back to the drive device, and the drive device drives the at least two light emitting units, respectively. The at least two light emitting units generate light sources with different color temperatures to compensate for each other.

Specifically, the at least two light emitting units are configured to compensate for the color temperature as follows. Firstly, the final color temperature parameter is determined, and a color temperature compensation solution is determined according to the final color temperature parameter. A lighting time of a cold light source and a lighting time of a warm light source are determined according to the color temperature compensation solution. A pulse width is determined by using the lighting time, and the color temperature is compensated for by changing the pulse width through the driver circuit.

Optimally, the drive device includes a processor and a driver circuit. The processor acquires the analysis result of the data acquisition and analysis unit and adjusts the magnitude or duty cycle of the drive current generated by the driver circuit. The drive currents input to the at least two light emitting units are different.

Specifically, the magnitude or duty cycle of the drive current is the analysis result obtained after the processor processes the to-be-analyzed data obtained from the data acquisition and analysis unit, namely the final color temperature parameter. Multiple color temperature compensation solutions are determined according to the final color temperature parameter, so that users can determine the color temperature compensation solution according to actual energy saving requirements, personal preference, or the need for convenient pulse modulation.

Optimally, the data acquisition and analysis unit includes a light detection unit, a visibility detection unit, a human body temperature measurement unit, and an environment measurement unit. The light detection unit detects the light intensity. The visibility detection unit detects the visibility value. The human body temperature measurement unit measures the body temperature of a user. The environment measurement unit measures the environment temperature.

Further, the data acquisition and analysis unit further includes an infrared movement signal detection unit. The infrared movement signal detection unit detects the presence or movement of the user, and converts an output signal into a voltage signal.

Further, the data acquisition and analysis unit is not limited to the above.

Optimally, the data acquisition and analysis unit sends the acquired data information to the processor. The processor calculates a color temperature parameter adapted to a current data state according to a built-in algorithm, and controls the driver circuit to adjust the light sources.

Optimally, the lighting system for automatically adjusting the color temperature further includes a manual adjustment unit, and the manual adjustment unit is arranged between the light emitting units and the driver circuit.

Further, the manual adjustment unit can perform fine-tuning after the final color temperature parameter is determined. Each light emitting unit corresponds to one manual adjustment unit, or one manual adjustment unit simultaneously controls a plurality of light emitting units. The manual adjustment unit may be a potentiometer configured to change the resistance to change the magnitude of the drive current, thereby fine-tuning the final color temperature parameter.

Optimally, the lighting system for automatically adjusting the color temperature further includes an adjustment switch, and the adjustment switch is provided with two modes. Specifically, one mode is an automatic mode, in which the color temperature parameter is automatically determined through the light, the infrared movement signal, the visibility, the human body temperature and the environment temperature, and then the final color temperature parameter is fine-tuned through the manual adjustment unit. The other mode is a manual mode, in which users perform adjustments depending merely on their preference.

The embodiments in this specification are described in a progressive manner. Each embodiment focuses on the differences from other embodiments, and the same or similar parts of each embodiment can refer to each other. The device provided in the embodiment corresponds to the method provided in the embodiment and is thus described briefly. Thus, the relevant parts of the device can refer to the description of the method.

The above description of the disclosed embodiments enables those skilled in the art to implement or utilize the present invention. A variety of modifications to these embodiments will be obvious to those skilled in the art, and the general principles defined herein can be implemented in other embodiments without departing from the spirit or scope of the present invention. Therefore, the present invention is not be limited to these embodiments shown herein, but conforms to the widest scope consistent with the principles and novel features disclosed herein.

What is claimed is:

1. A lighting method for automatically adjusting a color temperature, comprising the following specific steps:
    obtaining a light intensity and an infrared movement signal to determine whether to start lighting;
    obtaining visibility information, constructing a current visibility model according to the visibility information to obtain a visibility, and determining a first color temperature parameter according to the visibility;
    obtaining human body temperature data, and adjusting the first color temperature parameter according to the human body temperature data to obtain a second color temperature parameter; and
    obtaining environment temperature data, and adjusting the second color temperature parameter according to the environment temperature data to obtain a final color temperature parameter.

2. The lighting method according to claim 1, wherein the visibility information comprises one or more of a solid particle concentration, a droplet concentration and an atmospheric pressure.

3. The lighting method according to claim 1, wherein the step of constructing the current visibility model specifically comprises the following steps:
    obtaining a data image and a visibility value according to historical data;
    inputting the data image and the visibility value into a neural network model;
    training the neural network model to obtain a weight of the visibility information; and
    obtaining the current visibility model according to the weight.

4. The lighting method according to claim 3, wherein a current visibility level is obtained according to the current visibility model, and the current visibility level is configured to match the first color temperature parameter.

5. A lighting system for automatically adjusting a color temperature, comprising light emitting units, a drive device, and a data acquisition and analysis unit; wherein
    at least two light emitting units are arranged;
    the data acquisition and analysis unit feeds an analysis result back to the drive device;
    the drive device drives the at least two light emitting units, respectively, wherein the drive device comprises a processor and a driver circuit; and
    the at least two light emitting units generate light sources with different color temperatures to compensate for each other, wherein the data acquisition and analysis unit comprises a light detection unit, a visibility detection unit, an infrared movement signal detection unit, a human body temperature measurement unit, and an environment measurement unit;
  wherein the light detection unit is configured for obtaining a light intensity;
  the infrared movement signal detection unit detects a presence or a movement of a human body and generates an infrared movement signal;
  the visibility detection unit is configured for obtaining visibility information;
  the human body temperature measurement unit is configured for obtaining human body temperature data; and
  the environment measurement unit is configured for obtaining environmental temperature data, and
wherein the processor is configured for:
obtaining the light intensity from the light detection unit and the infrared movement signal from the infrared movement signal detection unit to determine whether to start lighting;
obtaining visibility information from the visibility detection unit and constructing a current visibility model according to the visibility information to obtain a visibility, and determining a first color temperature parameter according to the visibility;
obtaining human body temperature data from the human body temperature measurement unit and adjusting the first color temperature parameter according to the human body temperature data to obtain a second color temperature parameter; and
obtaining environment temperature data from the environmental measurement unit and adjusting the second color temperature parameter according to the environment temperature data to obtain a final color temperature parameter, and
controlling the driver circuit to adjust the light sources based on the final color temperature parameter.

6. The lighting system according to claim 5, wherein
the processor acquires the analysis result of the data acquisition and analysis unit, and the processor adjusts a magnitude or a duty cycle of a drive current generated by the driver circuit; and
drive currents input to the at least two light emitting units are different.

7. The lighting system according to claim 5, wherein
the infrared movement signal detection unit converts an output signal into a voltage signal.

8. The lighting system according to claim 5, further comprising a manual adjustment unit, wherein
the manual adjustment unit is arranged between the light emitting units and the driver circuit.

\* \* \* \* \*